United States Patent
Lee et al.

(10) Patent No.: US 8,208,602 B2
(45) Date of Patent: *Jun. 26, 2012

(54) HIGH FLUX PHOTON BEAMS USING OPTIC DEVICES

(75) Inventors: Susanne Madeline Lee, Cohoes, NY (US); Peter Michael Edic, Albany, NY (US); Vanita Mani, Clifton Park, NY (US); Forrest Frank Hopkins, Cohoes, NY (US); Eberhard Neuser, Wunstorf (DE)

(73) Assignee: General Electric Company, Niskayuna, NY (US)

( * ) Notice: Subject to any disclaimer, the term of this patent is extended or adjusted under 35 U.S.C. 154(b) by 222 days.

This patent is subject to a terminal disclaimer.

(21) Appl. No.: 12/710,064

(22) Filed: Feb. 22, 2010

(65) Prior Publication Data

US 2011/0206187 A1  Aug. 25, 2011

(51) Int. Cl.
*H05G 2/00* (2006.01)
(52) U.S. Cl. .......................................... 378/119; 378/84
(58) Field of Classification Search ............... 378/84, 378/85, 87, 119, 134, 147
See application file for complete search history.

(56) References Cited

U.S. PATENT DOCUMENTS

| | | | |
|---|---|---|---|
| 5,192,869 A | 3/1993 | Kumakhov | 250/505.1 |
| 5,604,353 A | 2/1997 | Gibson et al. | 250/505.1 |
| 6,934,359 B2 | 8/2005 | Chen et al. | 378/84 |
| 7,366,374 B1 | 4/2008 | Lee et al. | 378/31 |
| 7,412,131 B2 | 8/2008 | Lee et al. | 378/31 |
| 7,508,911 B1 | 3/2009 | Lee et al. | 378/84 |
| 2005/0094271 A1 | 5/2005 | Hoghoj | 359/572 |
| 2005/0117239 A1 | 6/2005 | Hoghoj et al. | 359/883 |
| 2006/0018429 A1 | 1/2006 | Hoghoj et al. | 378/84 |
| 2006/0062351 A1 | 3/2006 | Yokhin et al. | 378/86 |
| 2009/0041198 A1* | 2/2009 | Price et al. | 378/147 |
| 2009/0147922 A1 | 6/2009 | Hopkins et al. | 378/140 |

OTHER PUBLICATIONS

Tournear et al., "Gamma-Ray Channeling in Layered Structures", IEEE, pp. 4282-4285, 2004.
U.S. Appl. No. 12/469,121, filed May 20, 2009, titled "Optimizing Total Internal Reflection Multilayer Optics Through Material Selection".

* cited by examiner

*Primary Examiner* — Courtney Thomas
(74) *Attorney, Agent, or Firm* — Scott J. Asmus

(57) ABSTRACT

A system for producing at least one high flux photon beam is provided. The system includes two or more photon sources configured to produce photon beams, and at least one first stage optic device coupled to at least one of the photon sources and providing at least one focused photon beam through total internal reflection, wherein at least one of the photon beams and the focused photon beams are combined at a virtual focal spot.

32 Claims, 8 Drawing Sheets

HIGH FLUX PHOTON BEAMS USING OPTIC DEVICES

BACKGROUND

The invention relates generally to re-direction of photon beams, and more particularly to systems and methods for producing high-flux photon beams Many imaging applications using photon radiation, such as X-ray radiation, require higher flux output to improve the signal-to-noise ratio in the measured data. Increasing X-ray flux may be accomplished, for example, by redirecting into usable directions X-ray radiation emitted by an X-ray source that would otherwise not contribute to the fidelity of the measured data. For example, energy-dispersive X-ray diffraction (EDXRD) may be used to inspect checked airline baggage for the detection of explosive threats or other contraband. Such EDXRD may suffer from high false positives due to poor signal-to-noise ratio in diffracted X-ray signals, which may stem from a variety of origins. First, the polychromatic X-ray spectrum used in EDXRD is produced by the Bremsstrahlung part of the source spectrum, which is inherently low in intensity. Second, X-ray source collimation may eliminate more than 99.99 percent of the source X rays generated, since these X rays are not directed toward the baggage volume under analysis. Third, some of the materials being searched for, e.g., explosives, may not diffract strongly, leading to diffuse peaks in measured X-ray spectra, as the materials are amorphous or polycrystalline. Fourth, the diffracting volume may be small due to the need to improve the resolving capability of the system. Most of these limitations arise from the type and configuration of threat materials being searched for in baggage and the nature of the X ray interaction with these materials, making all but the second limitation unavoidable.

At lower X-ray energies, such as 60 keV and below, increasing the polychromatic X-ray flux density at the material being inspected has been addressed by coupling hollow glass polycapillary optics to low powered, sealed-tube (stationary anode) X-ray sources. The glass comprises the low index of refraction material, and air filling the hollow portions comprises the high index of refraction material. Total internal reflection from these types of optics typically becomes vanishingly small at energy levels above 60 keV, due to non-optimal differences in the real and imaginary parts of the refractive indices of air and glass.

Further, such optics use the concept of total internal reflection to reflect X rays entering the hollow glass capillaries at appropriate angles back into the hollow capillaries, thereby channeling a solid angle of the source X rays into collimated or focused beams at the output of the optic. As used herein, the term "collimate" refers to the creation of approximately parallel beams of electromagnetic (EM) radiation from divergent EM beams. The divergence of the parallel beams is on the order of the critical angle for total internal reflection, which vary from a few mill-radians at around 20 keV to 0.01° and lower for energies above 60 keV. Only about one to two percent of an EM source's solid angle typically is captured by the input of such known optics. In addition, the use of air as the high refractive index material in capillary or polycapillary optics prevents such optics from being placed within a vacuum, limiting their potential uses.

Thus, a device that can collect more of the generated source photons than are currently used and redirect them into a specified volume would be desirable for improving the SNR of a variety of X-ray analysis techniques.

BRIEF DESCRIPTION

In one embodiment, a system for producing at least one high flux photon beam is provided. The system includes two or more photon sources configured to produce photon beams, and at least one first stage optic device coupled to at least one of the photon sources and providing at least one focused photon beam through total internal reflection, wherein at least one of the photon beams and the focused photon beams are combined at a virtual focal spot.

In another embodiment, a high flux photon beam system is provided. The system comprises two or more photon sources configured to produce photon beams, at least one first stage optic device coupled to at least one of the photon sources and providing at least one focused photon beam through total internal reflection, at least one virtual focal spot formed from the focused photon beam, and at least one second stage optic device coupled to the virtual focal spot and configured to generate a shaped photon beam.

In yet another embodiment, a system for producing high flux photon beams is provided. The system includes two or more photon sources configured to produce photon beams, wherein the photon sources include at least one non-diverging photon source, at least one diverging source, and combinations thereof, wherein at least one of the photon sources includes an optic device providing a focused photon beam through total internal reflection, and the focused photon beams are combined at a virtual focal spot.

In another embodiment, a system for producing at least one high flux photon beam is provided. The system includes at least two radioactive photon sources configured to produce photon beams, and at least one first stage optic device coupled to one or more of the radioactive photon sources and providing focused photon beams, or parallel photon beams, or combinations thereof through total internal reflection, wherein the focused photon beams, or parallel photon beams, or photon beams, or combinations thereof are combined at a virtual focal spot producing one or more shaped photon beams.

In yet another embodiment, a system for producing at least one high flux photon beam is provided. The system comprises two or more photon sources configured to produce photon beams combined at a virtual focal spot, and at least one optic device coupled to the virtual spot and configured to generate a shaped beam comprising one of a parallel beam, focused beam, diverging beam, a fan-shaped cone beam, a stacked fan-shaped parallel beam, or combinations thereof.

These and other advantages and features will be more readily understood from the following detailed description of various embodiments of the invention that is provided in connection with the accompanying drawings.

DETAILED DESCRIPTION

Figure 1:
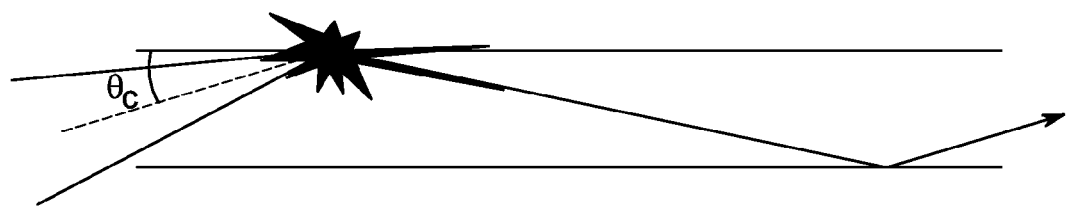
FIG. 1 is a schematic view illustrating the concept of total internal reflection.

The invention relates generally to re-direction of photon beams, and more particularly to systems and methods for producing high-flux photon beams. In certain embodiments, a system produces at least one high flux photon beam of higher flux than produced by existing laboratory-based X-ray sources. The system comprises two or more photon sources configured to produce photon beams. The system further comprises at least one first stage optic device coupled to at least one of the photon sources and providing at least one focused photon beam through total internal reflection, wherein at least one of the photon beams and the focused photon beam are combined at a virtual focal spot.

To more clearly and concisely describe the subject matter of the claimed invention, the following definitions are provided for specific terms, which are used in the following description and the appended claims. Throughout the specification, exemplification of specific terms should be considered as non-limiting examples.

As used herein, substantially non-diverging sources refer to sources with less than 1° of beam divergence.

As used herein, the term "first stage optic device" refers to one or more optic devices that are disposed in operative association with respect to the photon sources and focus photons from the photon sources to a virtual focal spot. As used herein, the term "second stage optic device" refers to one or more optic devices that are disposed in operative association with respect to the virtual focal spot where the virtual focal spot is possibly produced by the first stage optic device) to produce a shaped photon beam. Simply, the first stage optic device is disposed between the photon sources and the virtual focal spot, and the second stage optic device is disposed adjacent to divergent photon beams emanating from the virtual focal spot, in the direction away from the photon sources.

The terms "multilayer optics" and "optic device" may be used interchangeably throughout the application. The optic device may be made by employing the techniques disclosed in the commonly assigned application titled "OPTIMIZING TOTAL INTERNAL REFLECTION MULTILAYER OPTICS THROUGH MATERIAL SELECTION" having application Ser. No. 12/469,121. In certain embodiments, the first stage optic device may be configured to transmit photons from one or more distributed photon sources and focus such photons to a virtual focal spot as a focused photon beam, and the second or subsequent stage optics may then collect the photon beams from the virtual focal spot and transmit the photon beam in a desired shape depending on the type of application. Non-limiting examples of a shaped beam so produced by the second stage optic device may include a parallel beam, focused beam, diverging beam, fan-shaped cone beam, stacked fan-shaped parallel beam, and combinations thereof. It should be noted that the first stage optic device may be a TIR (total internal reflection) optic device, and the second stage optic device may be either a TIR optic device or a diffraction optic device.

The photon sources may comprise two or more photon sources, wherein the photon sources include at least one diverging photon source or at least one substantially non-diverging photon source and combinations thereof. Non-limiting examples of the diverging photon sources may include at least one radioactive source, an electron impact X-ray source, or a triboluminescent X-ray source and combinations thereof. The substantially non-diverging photon sources comprise at least one of an X-ray laser, a synchrotron radiation source, or a cyclotron radiation source, and combinations thereof. The combination of photon sources may depend on the desired beam shape, beam intensity, and beam energy composition (such as monochromatic, or polychromatic). The output of the virtual focal spot defines beam shapes comprising diverging beams.

As will be described in detail herein, high photon flux (such as X-ray flux) is desirable in certain imaging applications. However, such high photon flux at the interrogated volume may not be feasible. For example, in electron-impact X-ray tube technology, when the electron beam impinges on the target, the target material is heated. Thus, the electron beam power density must not exceed the power level that heats the target to its melting point or at which the source will cease to operate. This upper bound on the electron beam power density effectively determines the maximum number of X rays that a source can generate. To obtain more X-ray flux impinging on the interrogated volume, more X rays need to be generated. The present application describes a method for producing high flux photon beams, such as X-ray beams, without causing target material failure.

Selection of a plurality of a single type of photon source, or a combination of two or more types of photon sources, may depend upon the desired properties of the resultant high-flux photon beam. For example, for a high-flux monochromatic beam, it may be desirable to employ a plurality of single-type photon sources that will produce photons of similar energy ranges. Alternatively, a combination of different types of photon sources that produces photons in the same energy range may be used. However, if a polychromatic energy photon beam is desired then a combination of photon sources may be employed to produce a desired polychromatic photon beam. For example, a combination of two or more kinds of radioactive sources that emit photons of different energies may be employed to create a polychromatic beam, which has nearly discrete energy components. In one embodiment, the radioactive source may employ radioactive materials such as, but not limited to, strontium 90 and cobalt 60. In certain embodiments, the radioactive source comprises two or more materials. The two or more radioactive materials may consist of one or more radioisotopes. In certain embodiments, the system for producing the high flux photon beam may include at least two radioactive photon sources for producing photon beams. A first stage optic device may be coupled to one or more of these radioactive photon sources and provide focused beams or parallel photon beams and combinations thereof, through total internal reflection, wherein the focused photon beams or the parallel photon beams or the photon beams (from the radioactive sources) are combined at a virtual focal spot producing one or more shaped photon beams. In one embodiment, a first stage optic device may be coupled to each of the radioactive photon sources. In one example, two or more first stage optic devices may be coupled to a single radioactive photon source to desirably focus the photon beam from the radioactive source to the virtual focal spot.

In certain embodiments, combinations of different sources may provide a high flux photon beam of a desired energy spectrum for spectral imaging. As used herein, spectral imaging includes scenarios comprising a discrete energy distribution as well as multi-energy distributions. Multi-energy X-ray imaging, sometimes referred to as dual-energy imaging or energy discrimination imaging, has been shown to furnish information on specific material properties in scanned objects for security, industrial, and medical applications. Such energy discrimination imaging can be achieved in several ways, including the use of two or more different X-ray spectra, which is often the most feasible approach. A challenge lies in the sequential nature of such an examination, where projection data are collected, for example, first with one spectrum and then with another spectrum.

In one technique, an object of interest is scanned twice. A first complete projection data set is produced in the first scan for one energy and then a second complete projection data set is produced in the second scan for the second energy. For many dynamic or high throughput applications where imaging scenarios may preclude repetitive scanning, the logistics of physically scanning an object twice may be unacceptable. In such embodiments, two operating voltages of the source may be repeatedly switched to change the energy composition of the resultant photon beam. For example, for dual-energy scanning, a first accelerating potential in an X-ray tube is used to generate an energy spectrum for collection of a projection view, and the voltage is rapidly switched to a second voltage level to generate a second energy spectrum for collection of a second projection view. This topology complicates the X-ray tube/generator design. Alternatively, a single polychromatic energy spectrum can be used in conjunction with an energy-sensitive detector that characterizes the energy of each detected photon. However, fabrication of high-quality detector material for measuring high-flux X-ray beams is still a formidable technical challenge. Multilayer optics or optic device can shape energy spectrum as described in detail in U.S. patent application Ser. No. 11/952,498 titled "A MULTI-ENERGY IMAGING SYSTEM AND METHOD USING OPTIC DEVICES".

In certain embodiments, a first stage optic device may be configured to collect the photons from focal spots of the two or more distributed photon sources. The optic devices redirect the photons to produce a photon beam selected from the group consisting of a quasi-parallel beam, a slightly focused beam, a highly focused beam, a slightly diverging beam, and a highly diverging beam.

In certain embodiments, the first stage of optic devices may be configured to focus the photon beams emitted from the focal spots of the two or more photon sources to one or more virtual focal spots. The first stage optic devices may be coupled to one or more diverging photon sources to focus the photon beams from the diverging sources to one or more virtual focal spots. In certain embodiments, a second stage optic is coupled to one or more virtual focal spots and configured to redirect the photons from the one or more virtual spots to produce a desired beam shape. As will be described in detail with regard to FIG. 7, in one embodiment, additional photon sources may be employed to generate the additional focal spots. The photon beams from the photon sources and/or the focused photon beams from the first stage optic devices are combined to form the two or more virtual focal spots. A second stage optic device comprising an optic array of optic devices may be employed at the additional focal spots to produce a shaped beam.

In one embodiment, the first stage optic device may be coupled to at least one substantially non-diverging source to focus the photon beams to the virtual focal spot. In another embodiment, the substantially non-diverging photon sources may simply be oriented to direct the photon beams of the substantially non-diverging photon sources to the one or more virtual focal spots. In one example, photon beams from two or more substantially non-diverging photon sources may be combined at a virtual focal spot, and the optic device (second stage optic device) may be used to shape the beam. That is to say, in this embodiment, the second stage optic device may be employed without employing the first stage optic device.

In certain embodiments, the phenomenon of total internal reflection (TIR) is utilized. Referring to FIG. 1, total internal reflection occurs when a photon angle of incidence is less than a critical angle θc. Among other factors, the critical angle $θ_c$ for total internal reflection depends on the material, the difference in the relative indices of refraction, and the energy of the incident photons.

Figure 2:
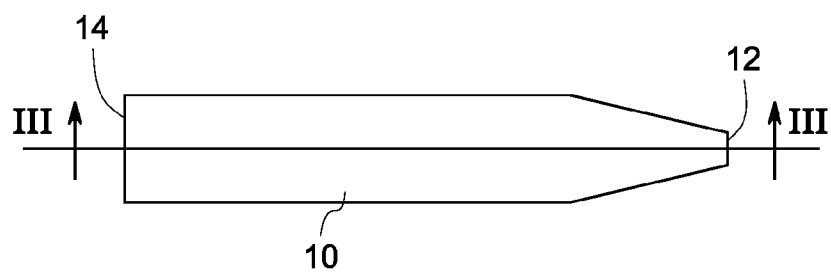
FIG. 2 is a top or side schematic view of an optic device constructed in accordance with one embodiment.
Figure 3:
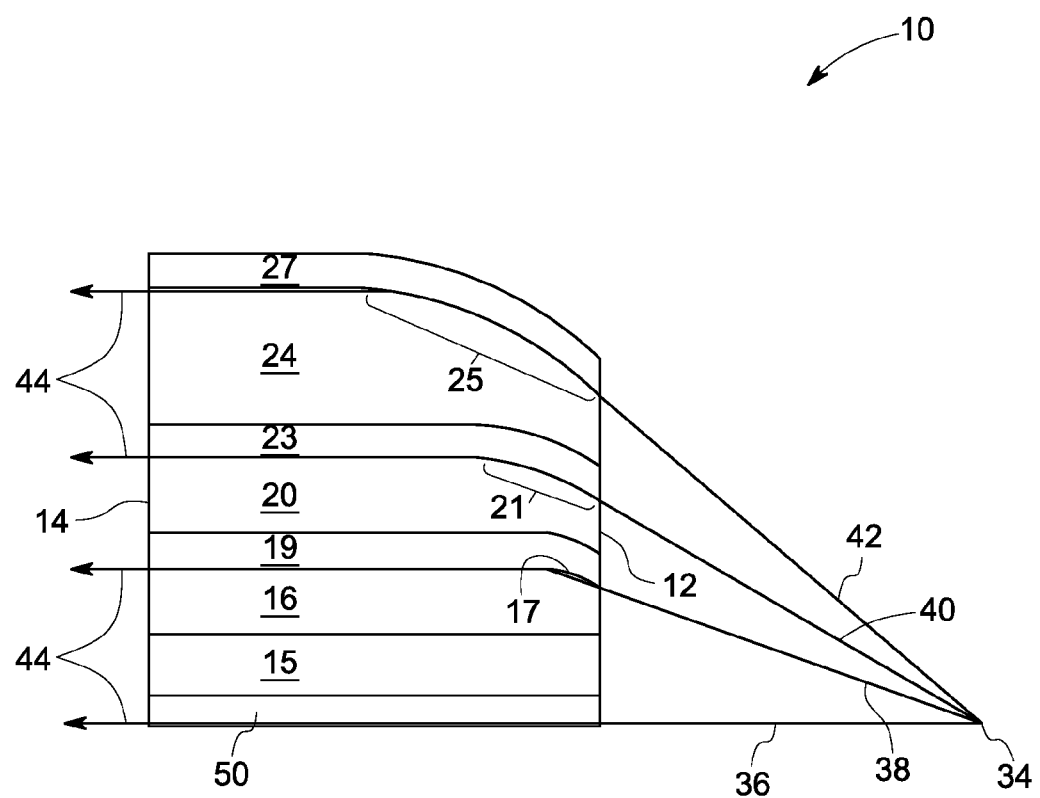
FIG. 3 is a radial profile of the optic device of FIG. 2 above the line III-III.

Referring now to FIGS. 2-3, there is shown a multilayer optic as described in U.S. Pat. No. 7,412,131, incorporated herein by reference. The multilayer optic 10 includes an input face 12 and an output face 14. By "multilayer" is meant a structure that has a plurality of monolayers with each layer having a single composition. In certain embodiments, the layers can be compositionally graded. As shown more particularly in FIG. 3, the multilayer optic 10 includes multiple layers of material, each having a different index of refraction. For example, there are layers 16, 20, and 24 surrounding a core 50. Layer 16 is positioned radially exterior to core 50. The core 50 may be formed of a higher index of refraction material such as beryllium, lithium hydride, magnesium, or any other suitable elements or compounds having similarly higher refractive indices and high X-ray transmission properties. The core 50 may be less than a micrometer to greater than one centimeter in diameter. Layer 20 is positioned radially exterior to layer 16 and radially interior to layer 24.

The materials selected for the various layers of the first stage or second stage or both optic stages have reflective properties such that their total internal reflection is maximized for each of the multilayer zones within the multilayer optic device. The optic device may be configured to receive and transmit photons of varying energies. In one embodiment, the photons have energy above 1 keV.

By using graded lower to higher index of refraction materials with concurrent graded higher to lower X-ray absorption properties, respectively, in contiguous layers, the multilayer optic 10 can reflect electromagnetic radiation through the principle of total internal reflection as described in detail in U.S. patent application Ser. No. 12/469,121 titled "OPTIMIZING TOTAL INTERNAL REFLECTION MULTILAYER OPTICS THROUGH MATERIAL SELECTION". Specifically, diverging electromagnetic radiation beams 38, 40, and 42 comprising photons and stemming from an electromagnetic radiation source 34 enter the input face 12 and are redirected into quasi-parallel beams of photons 44 exiting the output face 14. The cylindrical surface comprises one of a convex or a concave curvature along a longitudinal axis of the optic device. At least a portion of the input face for receiving input has one of a flat surface, a skewed surface, a convex surface, a concave surface, or a complex curved surface.

The composition of materials making up the multilayer optic 10, the macroscopic geometry of the multilayer optic 10, the thickness of the multilayer optic 10, and the number of individual layers determine the angular acceptance range of the multilayer optic 10. As used herein, the term "angular acceptance range" refers to angular selectivity of the optic such that incident photon beams within the angular acceptance range are reflected by the optics, but photon beams in an angular range outside the acceptance range are not redirected by the optics. The angular acceptance range may be from about 0 steradians up to about 2π steradians of a solid angle of a source of the photons. For ease of illustration, only a few layers have been illustrated with reference to multilayer optic 10. However, it should be appreciated that any number of layers, including into the hundreds, thousands, or millions of layers, can be fabricated to utilize total internal reflection to form the various types of photon beams listed previously.

Another feature of the multilayer optic 10 is that the core 50 and the layers 16, 20, 24 have photon redirection regions. The photon redirection segments 17, 21, and 25 are chosen to allow for the diverging electromagnetic radiation beams 38, 40, and 42 to be made parallel or near parallel as shown in FIG. 3, or conversely to allow for parallel or converging electromagnetic radiation beams to be made diverging (not shown), or for the diverging beams to be made converging. The minimum thickness of the photon redirection segments is determined by the minimum thickness that can be formed into a contiguous layer, which is at least two atomic layers, or about ten angstroms. The photon redirection segments 17, 21, and 25 may be chosen such that they each have a constant curvature. The curvature of each redirecting segment may be the same as or different from the curvatures of other redirecting segments. If each of the redirecting segments for a particular photon redirection region is straight, then the radius of curvature is infinite. In one example, layer 16 has a photon redirection segment 17 stemming from a center of curvature; layer 20 has a photon redirection segment 21 stemming from a second center of curvature; and, layer 24 has a photon redirection segment 25 stemming from yet another center of curvature.

One feature of this optic 10 is that the layers can be made thin enough and the overall optic length (from input face 12 to output face 14) short enough that very little photon absorption occurs in the optic. This is unlike known optics, where the photon channel diameters are typically greater than 10 microns and the overall length is several centimeters long.

Another feature of the multilayer optic 10 is that the individual (solid) layers can be formed conformally on top of one another. The conformation of the layers enables the multilayer optic 10 to be utilized in a vacuum environment. Conventional TIR optics utilize air as the higher refractive index material and typically cannot be used in high-vacuum environments. Further, the multilayer optic 10 can be utilized in applications that operate at energy levels above 60 keV, such as, for example, radiographic and computed tomography (CT) medical imaging, high-energy X-ray diffraction, explosive detection, industrial X-ray, and cargo inspection, to name a few. Some of these applications may operate at energy levels as high as 450 keV.

Although the multilayer optic cross-section is represented by a cylindrical shape in the figures, it should be noted that other geometrical cross-sectional shapes are also envisioned in the present application. Also, the distance of the optics from the different photon sources may vary. The distance between the photon source and the optics may depend on the emittance angle of the photon beam from the source.

In some embodiments, placing a filter at the input or the output faces of the first or second stage optic devices will make the output radiation from these optics quasi-monochromatic. Quasi-monochromatic radiation is radiation within a limited wavelength range that is greater than the highly monochromatic range of diffractive monochromators, but less than the full Bremsstrahlung spectrum from an X-ray source. Alternatively, the materials and layer thicknesses forming the optic devices can be altered to control the output X-ray spectrum from the optics.

In embodiments employing electron impact X-ray sources as one of the photon sources, target materials for the one or more X-ray production targets can be chosen from high-Z (atomic number) elements such as tungsten (W), or tantalum (Ta) to enhance X-ray production by the Bremsstrahlung process and to produce higher flux X-ray beams compared to targets of lower atomic number. Tungsten or tungsten-rhenium coated support metals such as molybdenum (Mo) or alloys of Mo can also be implemented. Rhenium alloying from 1-10% with heavy elements such as W helps render the target better able to handle the high temperatures generated by the electron beams colliding with the target. The heat generated upon electron impact can be extracted from the target by circulating cooling liquids through hollow passages in the one or more X-ray production targets to external heat exchangers. This arrangement allows continuous, high repetition rate, high power X-ray production without the attendant possibility of melting the target. When applying two or more electron impact X-ray sources, the target materials for the different sources may be same or different. Non-limiting examples of the electron generation mechanism in electron impact X-ray sources comprise at least one of spaced electron guns, spaced hot cathode-based electron guns, spaced cold cathode-based electron guns, or triboluminescent sources, each configured to impact a target material and produce at least one of the photon beams.

Since no material is required at the virtual focal spot where multiple X-ray beams are combined to create the high intensity X-ray beam, the X-ray flux density of the virtual focal spot is limitless, especially in comparison to target-based electron impact X-ray sources. Combining the output of the various photon sources (i.e., the photon beams) not only has an additive effect on the total output power of the source, but also allows comparatively lower power consumption than from a single source producing the same photon flux.

The desired size of the virtual focal spot may vary depending on various applications. In one embodiment, sub-micron sized focal spots may be used for ultra-high resolution CT. For example, the size of the virtual focal spot may be 20 microns or smaller. Non-limiting examples of applications of micron-sized focal spots may include inspection of printed circuit boards with multiple layers or imaging small cracks in manufactured parts. In diffraction applications, micron-sized focal spots may be used to map structural changes, such as stress and strain. In fluorescence applications, micron-sized focal spots may be used to map compositional changes on a fine scale. Focal spots on the order of 1 mm or larger may be used for radiography of large objects, such as a full torso, or an engine block.

Typically, conventional optics (e.g. diffractive and refractive) offer point-to-point focusing. In other words, the virtual focal spot produced using conventional optics can be no smaller than the diameter of the source focal spot. However, advantageously, the multilayer TIR optics are not limited in this regard because of the physics by which they reflect photons and their method of fabrication. It is this ability of taking a larger focal spot, combining multiple such focal spots, and creating a reduced-size virtual focal spot (less than a micron) having significantly higher flux density that may enhance the speed with which industrial high-resolution CT is performed.

The present application combines multiple sources into a single virtual focal spot of higher intensity than that from any of the individual sources. Thus, this virtual focal spot could be used in any of the applications listed above to decrease the data acquisition time. Additionally, having the focal spot offset from the source housing is an advantage in industrial high-resolution CT, where the object is rotated and the source and detector are fixed in space (in medical CT, the patient is stationary while the source and detector rotate around the patient). Currently available sources are relatively weak, which require the object be placed as close to the X-ray source as possible to obtain reasonable data acquisition times. However, there are limitations on the minimum distance between the object and the source; the object and the source cannot be placed closer than a certain distance due to the object's physical boundaries interfering with the source housing when the object is rotated. The virtual focal spot eliminates the interference issue, while the combination of multiple sources eliminate the need to be as close as possible to the X-ray source because of the higher intensity of the combined sources.

Multilayer optics in accordance with embodiments of the system can collect a large solid angle of a photon source and redirect polychromatic energies into shaped beams, such as quasi-parallel photon beams. As used herein, the term "quasi-parallel" means that diverging beams of photons have been collected and focused into beams of electromagnetic radiation or photons to exit the output face 14 (FIG. 1) at or below the critical angle θc. This critical angle divergence causes the photon beam to be larger than the output face 14 of the optic 10. In the text that follows, the terms quasi-parallel and parallel will be used interchangeably. Alternatively, multilayer optics in accordance with embodiments of the system may be configured to produce shaped beams that are focused or diverging. In one example, the shaped beam may include a parallel beam, focused beam, diverging beam, fan-shaped cone beam, stacked fan-shaped parallel beam, and combinations thereof.

The combination of photon emittance from the same or different diverging and substantially non-diverging photon sources, or a combination of two or more of the same type of photon sources, using the multilayer optics provides a resultant photon beam having a desired energy spectrum, flux density, and beam shape to suit specific applications as described in detail below. Such energy spectra, flux densities, and beam shapes may be otherwise not possible to achieve using conventional systems. One feature of the system is the combination of two or more sources and using two multilayer optics to coalesce the radiation of these sources into a single photon beam with specifically engineered properties. The properties of the photon beam may be varied over time, by controlling the photon emission of the photon sources. For example, in a medical application, the energy of the resultant photon beam may be varied to suit the region of interest where the beam is being applied. The variation in the photon beam may enable the region of interest to be simultaneously or sequentially treated and/or imaged. The energy of the photon beam can be varied by switching off some of the photon sources for treating or imaging a certain region of interest, and subsequently switching on the previously inactive sources, for example, for treating or imaging a different region of interest.

In certain embodiments, at least one of the photon sources from the combination of sources may leverage the optic device. In these embodiments, other photon sources may be adapted to transmit photon beams to the virtual focal spot to which the optic device is configured to focus the photon beams. The different sources may employ the same or different optic devices. The arrangement of optic devices and photon sources may work either in vacuum or in air.

Figure 4:
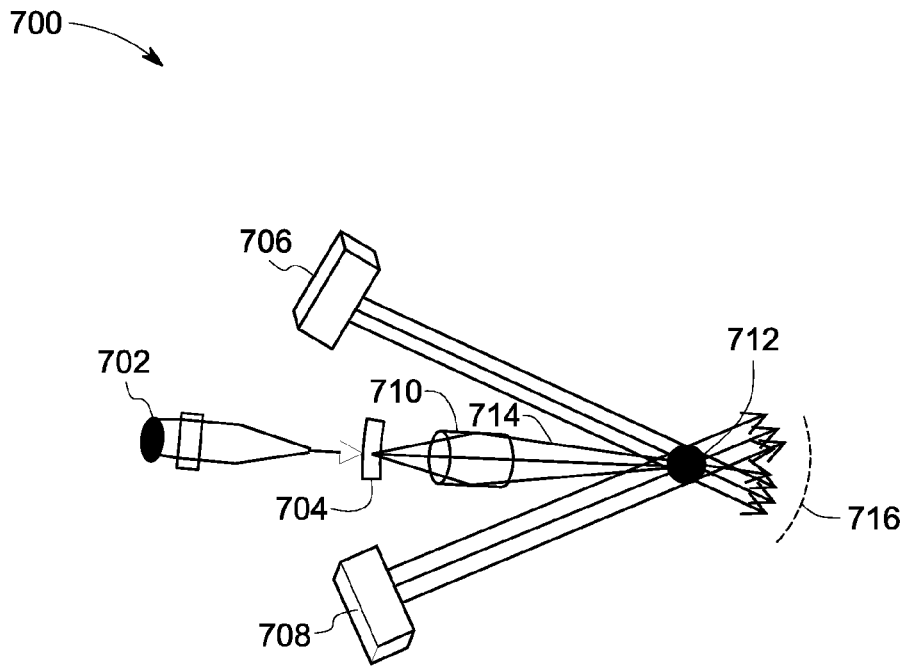
FIGS. 4-11 are schematic representations of combinations of photon sources and one or more optic devices to produce high flux photon beams of different shapes.

Referring to FIG. 4, a system 700 configured to produce a high flux photon beam in accordance with an exemplary embodiment of the system is illustrated. The system 700 includes two or more distributed photon sources, which can include an electron beam source 702 in combination with a target 704. The reference numerals 706 and 708 represent substantially non-diverging sources, such as an X-ray laser, a synchrotron radiation source, or a cyclotron radiation source. For example, the reference numeral 706 may represent a laser source and the reference numeral 708 may represent a cyclotron source. However, the desired embodiment is not limited to these configurations. The X rays from the target 704 are focused to the focal spot 712, which is spatially separated from the photon sources.

The electron beam generation mechanism inside the X-ray source 702 may be one or more of a micro-fabricated cathode carbon nanotube (CNT), high emissivity material nanorods (e.g. nanometer-diameter solid cylinders made from materials that produce electrons easily), high emissivity engineered multilayer-based field emitter cathode, or other cold cathode materials. Examples of field emitter electron sources may include CNTs anchored to a substrate, grown on catalyst islands with a chosen composition for enhanced output and life. In further exemplary embodiments, the electrons may be generated from other sources such as, but not limited to, thermionic emitters (e.g., hot tungsten wire, as in traditional X-ray source electron emitters), dispenser cathodes (e.g., modestly heated materials that produce electrons easily); and the like. In exemplary embodiments, electrons are extracted from the emitters (e.g., from the CNT or nanorod tips or the top layer of the multilayers) into the vacuum (i.e., the space). The electron guns are configured to accelerate the electrons to a high kinetic energy and to focus the electrons onto the one or more X-ray production targets. Although not shown, electron beam source 702 and target 704 are enclosed within a vacuum enclosure.

The X rays from the target 704 are directed at the focal spot 712 by the first stage optic device 710, which may or may not reside within the vacuum enclosure (not shown) housing the electron beam source 702 and target 704. Since the sources 706 and 708 are substantially non-diverging, the two sources 706 and 708 do not require a first stage optic device. The sources 706 and 708 may be oriented such that the beams of photons from the sources 706 and 708 intersect at point 712, which is also the virtual focal spot for the X-ray beams 714 after passing through the first stage optic device 710. Although not illustrated, the sources 706 and 708 may also employ a first stage optic device to converge the photon beams at the virtual focal spot 712.

The resultant outgoing photon beam represented generally by the reference numeral 716 is a divergent beam with different portions of the beam contributed by different photon sources, in which the different portions may overlap spatially. Such a photon beam 716 may be used in applications such as imaging and X-ray. Among other purposes, the distance between the optic devices and virtual focal spot may be based on the required position for the virtual focal spot.

Figure 5:
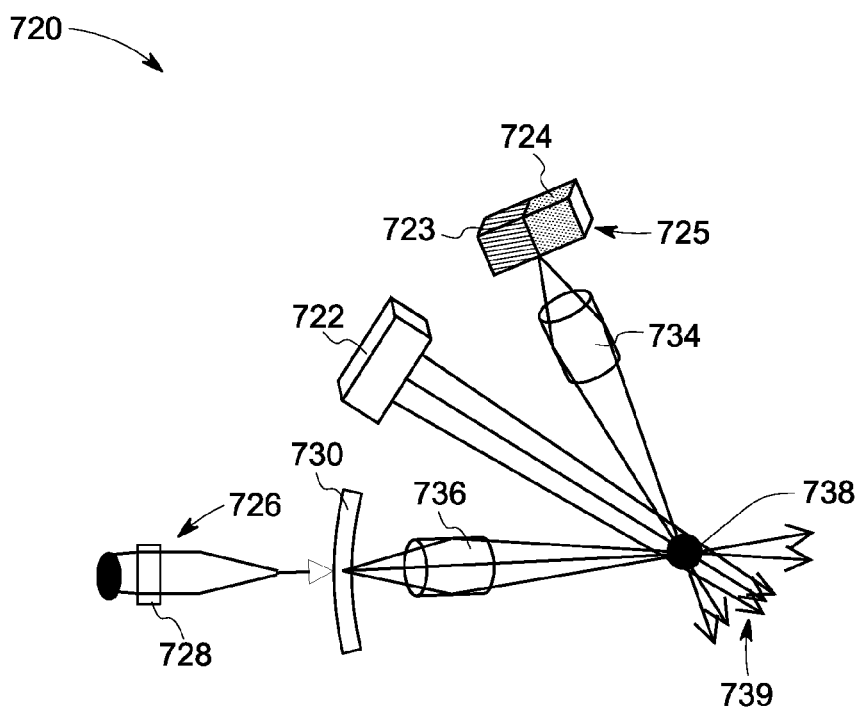

Referring now to FIG. 5, the system 720 produces a divergent beam 739. The system 720 includes a combination of diverging and substantially non-diverging sources. The diverging sources include a radioactive source 725 and an electron impact X-ray source 726. The radioactive source may include one material or a combination of different materials. In the illustrated example, the radioactive source 725 is a combination of two radioactive materials 723 and 724. In the illustrated embodiment, the two radioactive materials are disposed adjacent each other. However, the two radioactive materials may also be arranged in layers or form a mixture. The two different radioactive materials 723 and 724 may comprise one or more radioisotopes and may emit photons of different energies, thereby making the source 725 a polychromatic source.

The system 720 further includes an electron impact X-ray source 726 that is a combination of an electron source 728 and a target 730 positioned in a vacuum enclosure (not shown). The electron impact X-ray source 726 is the other diverging source besides the radioactive source 725. Further, the system 728 employs a substantially non-diverging source, such as an X-ray laser 722. The photon sources 725 and 726 employ first stage optic devices 734 and 736, respectively, to focus the photons to a virtual focal spot 738. Such a beam may be employed for treatment of a single localized tumor at the virtual focal spot. Although shown as comprising a substantially non-diverging source, an X-ray source, and radioactive sources, system 720 may comprise any combination of radiation sources. Although not illustrated, the substantially non-diverging source may also employ a first stage optic to focus the photons from the substantially non-diverging source to the focal spot 738.

The highly divergent beams of FIGS. 4 and 5 may find utility in non-destructive examination applications requiring an increased field-of-view, and in medical interventional imaging and treatments requiring an increased field-of-view, such as the imaging of large tumors. Additionally, the limited size of the virtual focal spot containing a high photon flux density may find great utility in treating localized tumors. For a smaller coverage area for the resultant beams of FIGS. 4-5, the intensity may be higher.

Figure 6:
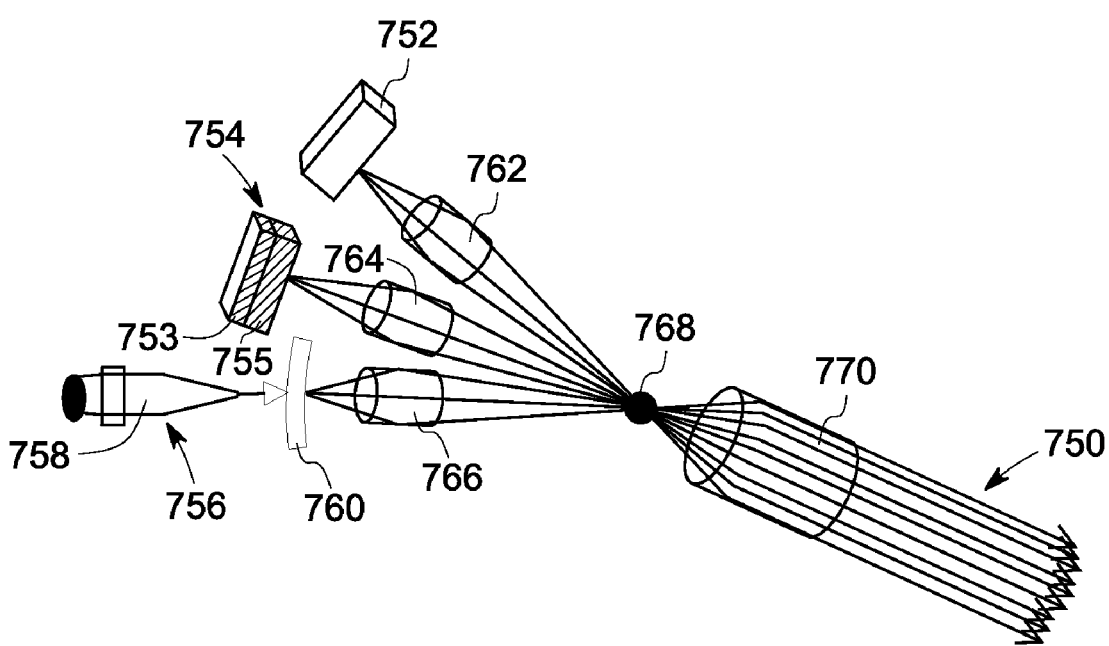
Figure 7:
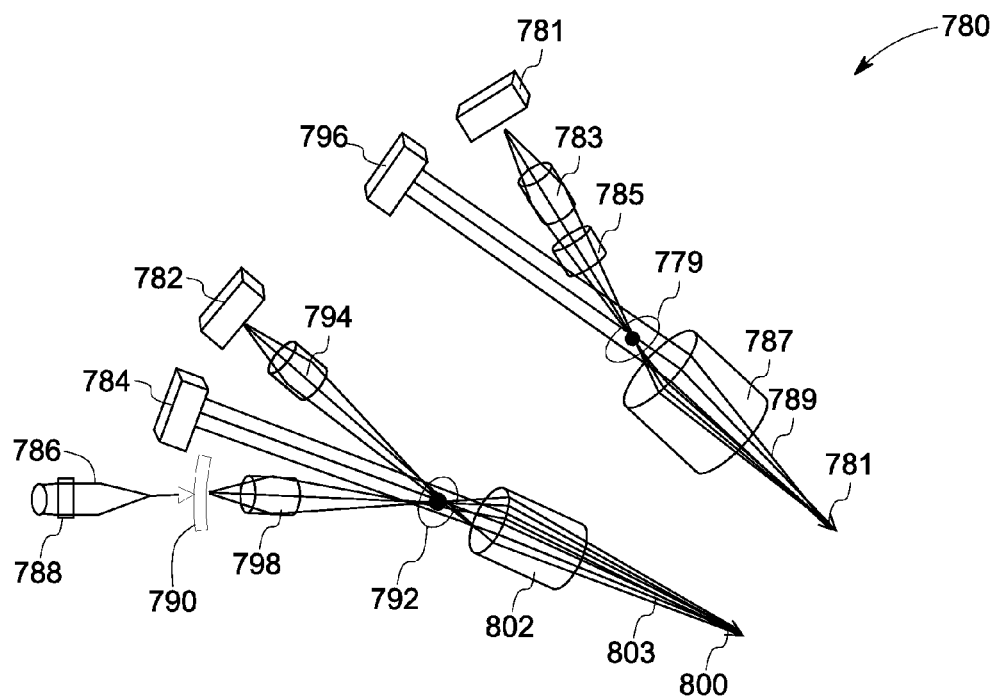
Figure 8:
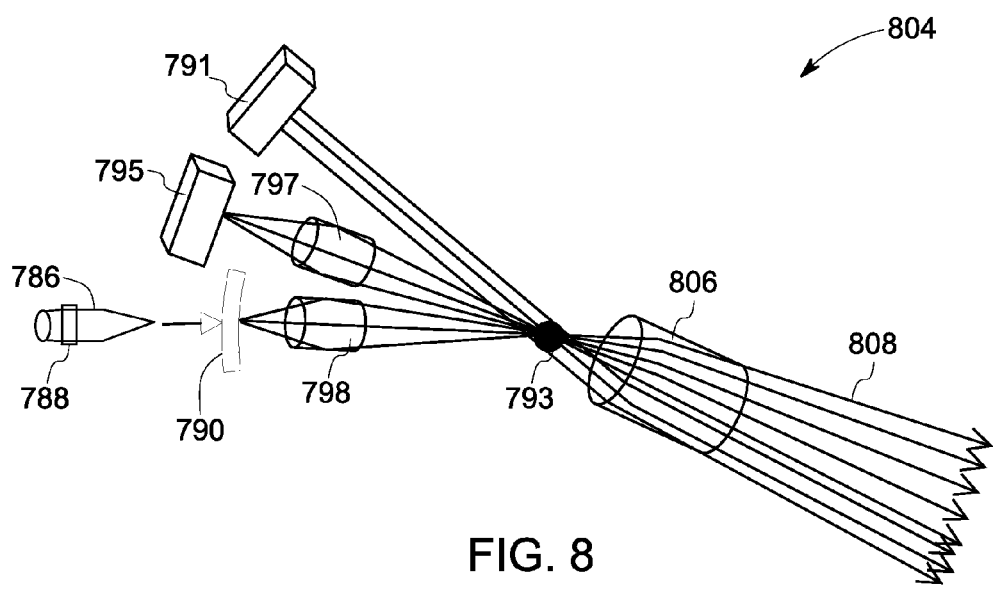

FIGS. 6-8 illustrate different exiting beam shapes, parallel (FIG. 6), focused (FIG. 7) and diverging (FIG. 8) for a combination of photon sources and two stage optic devices.

In the illustrated embodiment of FIG. 6, a parallel beam 750 is produced by employing all diverging photon sources in combination with two stages of optic devices. In the illustrated embodiment, the photon beam 750 may be produced by employing diverging photon sources, such as, a betatron radiation source 752, a radioactive source 754, or an electron impact X-ray source 756, The radioactive source 754 may include a combination of two radioactive materials 753 and 755, disposed in a layered arrangement, for example. The electron impact X-ray source 756 includes an electron source 758 and a target 760 positioned within a vacuum enclosure (not shown). The types of photon sources are not limited to the configuration shown; alternate embodiments utilizing any configuration of available radiation sources are envisioned. The photon sources employ two stages of optic devices. The first stage optic devices 762, 764 and 766 are focusing optics that focus the photons from sources 752, 754 and 756, respectively to a virtual focal spot 768. A second stage optic device 770 may be employed to collect the photons from the single virtual focal spot 768 and direct the photons as a single, high intensity, parallel beam 750. The optic device 770 may be disposed closer to the virtual focal spot 768 if the second stage optic device 770 has a large collection angle.

The resultant high intensity and high flux parallel photon beam 750 may be either monochromatic or polychromatic or combinations thereof. Although not illustrated, a filter may be disposed in operative communication with the optic device 770, for example, to filter out the unwanted wavelengths from the beam 750 to produce a monochromatic beam or, alternatively, the materials from which optic 770 are made can be selected to produce a limited range of photon energies.

Applications for such a high-intensity, high-flux parallel beam of photons include imaging, X-ray diffraction, and backscatter imaging. Alternatively, if the second stage optic device 770 is focusing, the resultant beam focuses to a point, with its diameter dependent on the output convergence angle of the second stage optic. Such a focused beam may find application in brachytherapy. In addition, a focused beam with a circular cross-section may find utility in X-ray diffraction, X-ray fluorescence, and non-destructive examination applications.

Referring to the arrangement of FIG. 7, the system 780 is employed to produce two focal spots 800 and 781 spatially separated. In the illustrated embodiment, at least one additional first stage optic device is coupled to the additional photon sources generating two or more virtual focal spots. The focal spot 800 is produced by employing diverging photon sources such as a betatron X-ray source 782, and an electron impact X-ray source 786, and a substantially non-diverging photon source, such as an X-ray laser 784. The electron impact X-ray source 786 includes an electron source 788 and a target 790 positioned within a vacuum enclosure (not shown). Photons from the three sources 782, 784 and 786 are directed to a virtual focal spot 792 using optic devices 794 and 798. The diverging photon source 782 uses a first stage optic device 794 to focus the photons to the virtual focal spot 792. As illustrated, the virtual focal spot 792 is not a point but a region, where the substantially non-diverging photon beams from the source 784 and the focused beams, after passing through the first stage optic devices 794 and 798, converge. The photons from the virtual focal spot 792 are focused to another focal spot 800 using a second stage optic device 802.

The focal spot 779 is produced by employing a substantially non-diverging photon source 796 and a diverging photon source 781. The diverging photon source uses two first stage optic devices 783 and 785 to focus the photons to the virtual focal spot 779. As illustrated, the virtual focal spot 779 may not be a point but a region as represented by the reference numeral 779, where the substantially non-diverging photon beams from the source 796 and the focused beams, after passing through the first stage optic devices 783 and 785, converge. The photons from the virtual focal spot 779 are focused to another focal spot 781 using a second stage optic device 787.

The highly focused beams 803 and 789 may find utility in X-ray fluorescence and non-destructive examination applications. However, to suit the applications, such as convergent beam X-ray diffraction for biological crystals, the second stage optic devices 802 and/or 787 may focus the photon beam with shallower convergence angles. The two beams 789 and 803 having different convergence angles may be used to simultaneously image or examine spatially separated locations in a subject.

As illustrated in FIG. 8, the system 804 employs a combination of diverging sources 795 and 786, and a substantially non-diverging source 791. The photon sources may employ first stage optic devices 797 and 798 to focus the beams from photon sources 795 and 786, respectively to a virtual focal spot 793. The second stage optic device 806 collects the focused photon beams from the optic devices 797 and 798 and the photon beams from the substantially non-diverging source 791 to form the divergent beam 808. The slightly divergent beam 808 facilitates greater coverage area for a sample that is being imaged or treated, for example. Once again, alternate system embodiments are envisioned that use any combination of irradiative sources.

Figure 9:
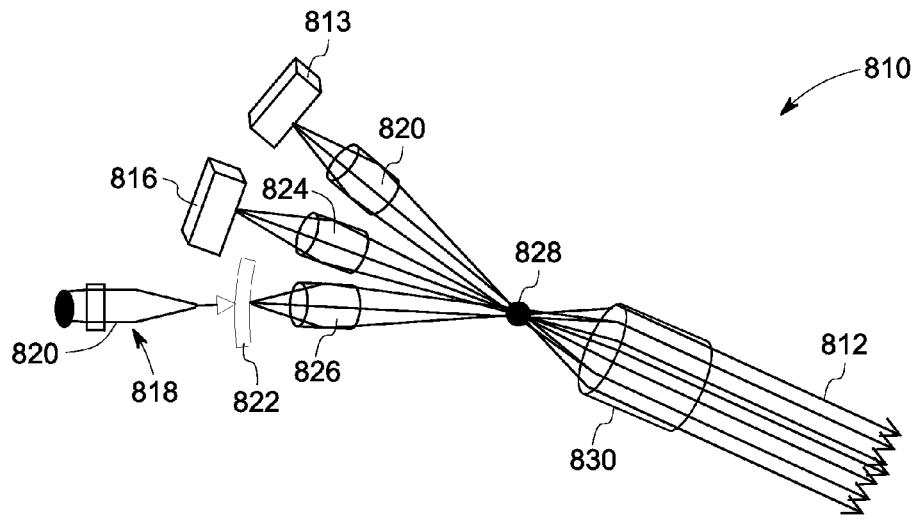

FIG. 9 illustrates a configuration of a system 810 configured to produce a high intensity, high flux parallel photon beam 812. The system 810 employs different diverging photon sources, such as a betatron radiation source 813, a radioactive source 816, and an electron impact X-ray source 818. The electron impact X-ray source 818 includes an electron source 820 and a target 822 positioned within a vacuum enclosure (not shown). Although shown as comprising a betatron radiation source, a radioactive source, and an electron impact X-ray source, the photon sources 813, 816 and 818 may include any other diverging or non-diverging sources. The photons from the sources 813, 816 and 818 are focused to a virtual focal spot 828 using first stage optic devices 820, 824, and 826, respectively. A second stage optic device 830 focuses the beams from the focal spot 828 into parallel beams 812.

Figure 10:
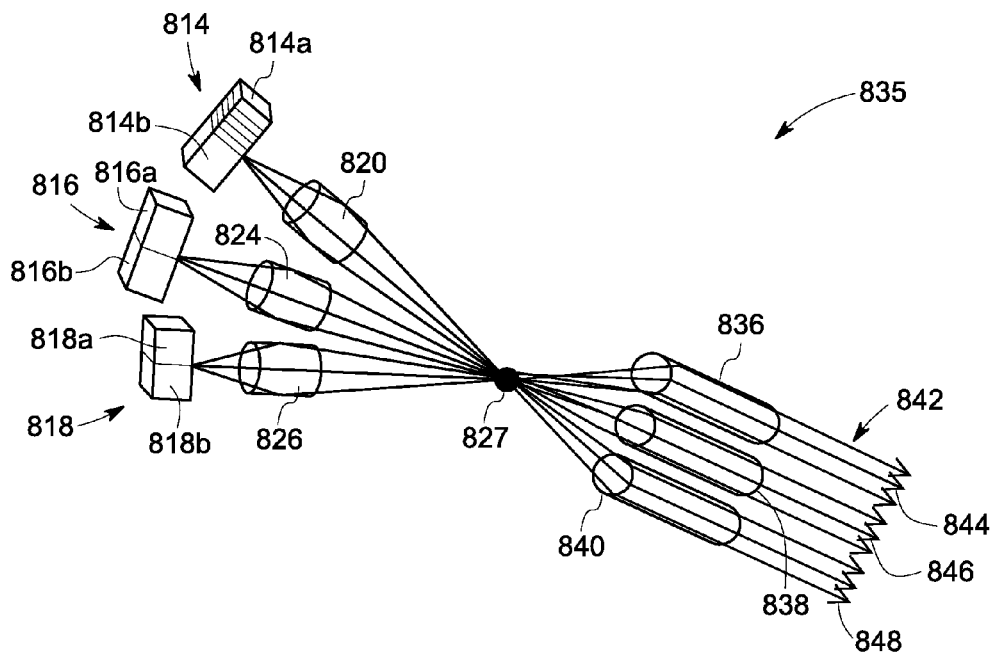

FIG. 10 illustrates an alternate embodiment of the system 810 of FIG. 9. In the illustrated embodiment, the system 835 employs radioactive sources 814, 816 and 818. Each of the radioactive sources 814, 816 and 818 comprise two radioactive materials, 814a and 814b, 816a and 816b, and 818a and 818b, respectively. In the illustrated embodiment, the system 835 employs an array of second stage optic devices 836, 838 and 840 to form a parallel beam 842 that comprises three sets of parallel beams 844, 846 and 848. Each of the beams 844, 846 and 848 may contain a different energy beam, or a combination of different energies. The energies of the beams 844, 846 and 848 may be selected by using specific optic component materials and optic geometrical designs in the second stage optics 836, 838, 840 and/or filters appropriately chosen to shape the X-ray spectra. Although shown as providing output beams that are quasi-parallel, systems 810 (FIG. 9) and 835 (FIG. 10) comprising multiple optic devices may provide output beams that are quasi-parallel, slightly converging, highly converging, slightly diverging, or highly diverging—or combinations thereof, since multiple optic devices shape the exiting beams 812 and 842, respectively.

Figure 11:
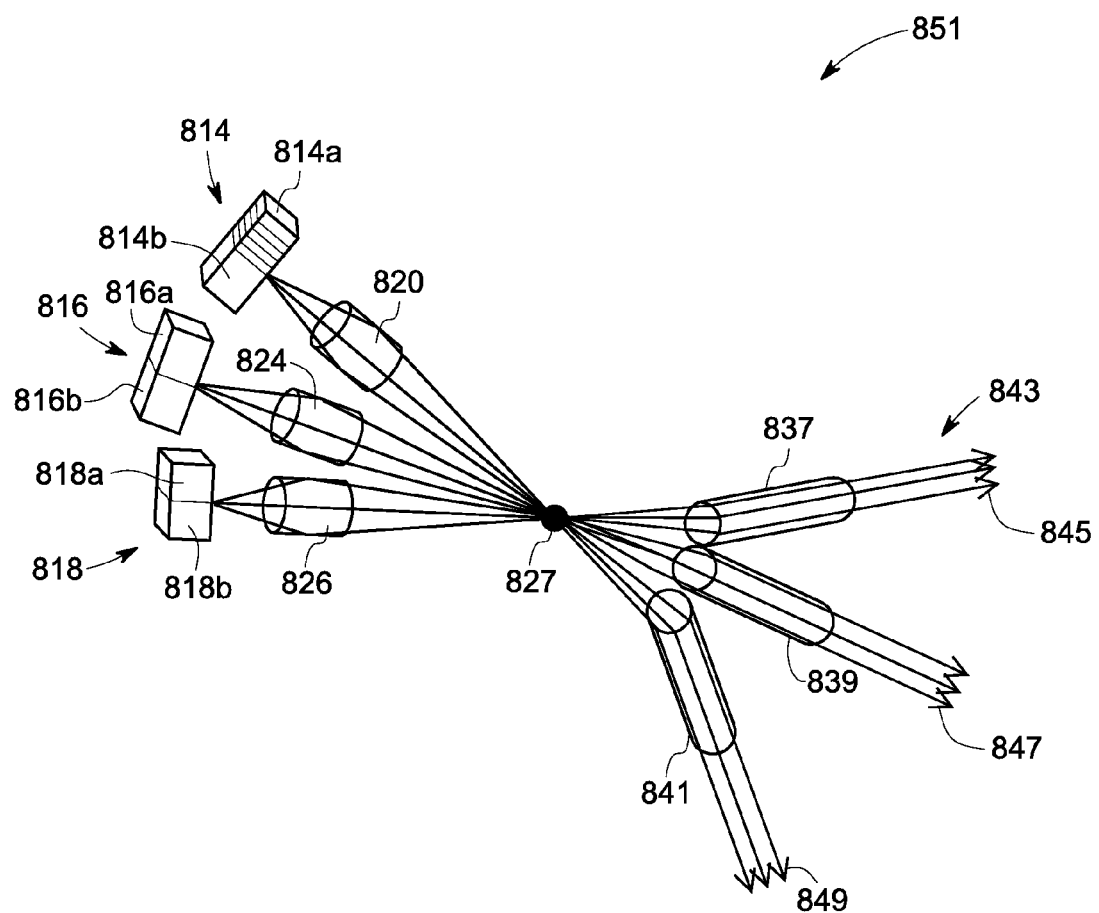

FIG. 11 illustrates an alternate embodiment of the system 835 of FIG. 10. In the illustrated embodiment, the system 851 employs an array of second stage optic devices 837, 839 and 841 to form a beam 843 that comprises three sets of parallel beams 845, 847 and 849. Each of the beams 845, 847 and 849 may contain a different energy beam, or a combination of different energies. The energies of the beams 845, 847 and 849 may be selected by using specific optic component materials and optic geometrical designs in the second stage optics 837, 839, 841 and/or filters appropriately chosen to shape the X-ray spectra. The distance between the sets of parallel beams 845, 847 and 849, within the beam 843 may be varied to suit the application, such as distribution of the treatment/imaging sites.

In one embodiment, the single virtual focal spot may be the source of photons for the application, with a standard slit (e.g., the slit used in CT medical imaging) or pinhole mechanical collimator (e.g., the standard collimator used in x-ray diffraction) to produce the desired beam shape. In another embodiment, a second stage of photon optics may replace the mechanical collimator to create a single, intense, highly parallel, X-ray beam from the virtual focal spot. The minimum focal spot size can generally be determined by the accuracy with which each photon optic can be mechanically aligned with the common virtual focal spot and the smallest focal spot size each photon optic can produce. In exemplary embodiments, the photon beam collimator is configured to receive and redirect X-ray beams, such as photon beams, of high energy (e.g., 40 keV-450 keV or higher). In exemplary embodiments, the focusing photon optics may or may not be contained inside the vacuum housing. In exemplary embodiments, the mechanical collimator or collimating optics at the virtual focal spot may or may not be contained inside a vacuum housing.

Optionally, a collimator may be used to collimate the photons from the virtual focal spot to generate a collimated photon beam. The collimator may comprise at least one of a z collimator, a diffracting single crystal, a grazing incidence diffraction-based X-ray optic, a multilayer total internal reflection-based X-ray optic, a total external reflection-based X-ray optic, and a refraction-based X-ray optic mechanically aligned with the virtual X-ray focal spot and configured to create the collimated X-ray beam.

The different photon sources may or may not be disposed in a vacuum. In exemplary embodiments, the electron beams (as well as the emitter source), the electron guns, the low-emittance electron beam optics, and the one or more X-ray production targets, comprising one or more photon sources, are all located in vacuum chambers held at pressures of about $10^{-9}$ mbar to $10^{-4}$ mbar.

Although not illustrated, in some embodiments each source spots may have an array of optic devices to collect more of the source spot and redirect it to one or more virtual focal spots. In these embodiments, another optic may or may not be placed to create another convergent or divergent beam.

In the illustrated embodiments of FIGS. 4-10, the combinations of different photon sources to produce different beam shapes are examples of several combinations that are possible. The illustrated examples are for understanding purposes and should not be construed as limiting the system.

One example of the utility of multilayer TIR optics formed to emit a variety of beam shapes is in medical interventional treatments, such as treatment of tumors, where the optic output beam shape can be matched to the tumor shape. Such multilayer TIR optics would allow X rays to be focused onto the tumor without irradiating nearby healthy tissue, providing targeted treatment with a minimum of damage to surrounding healthy tissue.

Multilayer TIR optics formed to emit a fan beam in one plane that is slightly or highly diverging in the direction transverse to the fan beam plane may find utility in medical interventional applications, such as close-up imaging to increase field-of-view or conventional CT imaging. The divergence in the direction transverse to the fan beam plane may be less than, equal to, or greater than the source divergence. Multilayer TIR optics formed to emit a fan beam in one plane that is quasi-parallel, slightly focusing, highly focusing, slightly diverging, or highly diverging perpendicular to the plane of the fan may find utility in computed tomography, X-ray diagnostic, and non-destructive examination applications. The fan beam may have a divergence the same as, less than, or greater than that of the source.

A multilayer TIR optic coupled to a diffracting crystal may produce a parallel monochromatic fan beam that may find utility, provided the intensity is great enough, in medical imaging and interventional treatments. Such monochromatic imaging would reduce a patient's dose of X rays while increasing the resolution, for example, by reducing cone beam artifacts, and reducing streaking/shading such as those incurred with beam hardening effects. Alternatively, appropriate material selection in the multilayer TIR optic coupled with the proper optic design can produce the quasi-parallel monochromatic fan beam.

Backscatter imaging, X-ray diffraction, X-ray fluorescence, radiography, and computed tomography (CT) imaging for security, industrial inspection, and healthcare may be some of the applications for the beam shape of photon beam 843 of the arrangement 851 of FIG. 11. One of the applications, for the three parallel sub-beams 845, 847 and 849 may be for simultaneously imaging multiple locations in a subject. In another example, beam 843 may be employed for targeted tumor treatment with different X-ray energies or the same depending on the size and distribution of tumors. The beam shape of beam 843 reduces dose to healthy tissue. For example, if a regular fan-shaped beam having a coverage area as broad as that of beam 843 is employed for the targeted tumor treatment, the healthy tissues disposed between the beams 845 and 847, or 847 and 849 would unnecessarily have to be exposed to be radiation. Whereas, the beam shape of beam 843 avoids such unnecessary exposure of the healthy tissues. Further, the distance between the sub-beams 845, 847 and 849 may be tailored by selecting appropriate optical devices 837, 839 and 841. Further, the intensity of the beam 843 may be increased by reducing the coverage area and moving the sources closer together.

Applications for such photon beams as described above could be in several different fields, such as a targeted imaging system, a diffraction-enhanced imaging system, a phase contrast imaging system, a brachytherapy system, a computed tomography system, a radiography system, a backscatter imaging system, a radio-isotope radiography system, an X-ray diffraction system, an X-ray fluorescence system, or combinations thereof. Due to the tissue penetrating property, gamma rays (radiation from radioactive material) or X rays have a wide variety of applications such as in imaging, radiation therapy, and sterilizing purposes. For example, medical equipment is typically sterilized before use to remove decay-causing bacteria. This method may also be employed to remove harmful bacteria from food or for preventing fruits and vegetables from sprouting to maintain freshness and flavor. In addition, as a form of ionizing radiation, the gamma rays and X rays have the ability to effect molecular changes. The molecular changes may be used to alter the properties of semi-precious stones, and is often used to change white topaz into blue topaz. Gamma rays may be used to treat some types of cancer by providing multiple concentrated beams of gamma rays that are directed on the growth in order to destroy the cancerous cells. The sub-beams may be aimed from different angles to focus the radiation on the growth while minimizing damage to the surrounding tissues. As discussed above, with the help of the optic devices, the beam shapes, distribution of sub-beams within a beam may be tailored to suit the application requirements. Radioactive elements may be employed in the medical field, for sterilization of medical instruments, for example. Also, radioactive elements may be employed in the food and hygiene industry. By subjecting the medical instruments or food to concentrated beams of radiation, harmful microorganisms that typically cause contamination and disease can be killed. A high energy and high flux radiation beam is desired to decrease the contamination and process time of such sterilization processes.

In addition, electromagnetic radiation sources, such as, radioactive elements, are commonly employed in the manufacturing industry for nondestructive testing to monitor materials and processes during or post manufacturing of products. Radiography is employed to image materials and products during various stages of manufacturing to check for any internal failures or damage.

Figure 12:
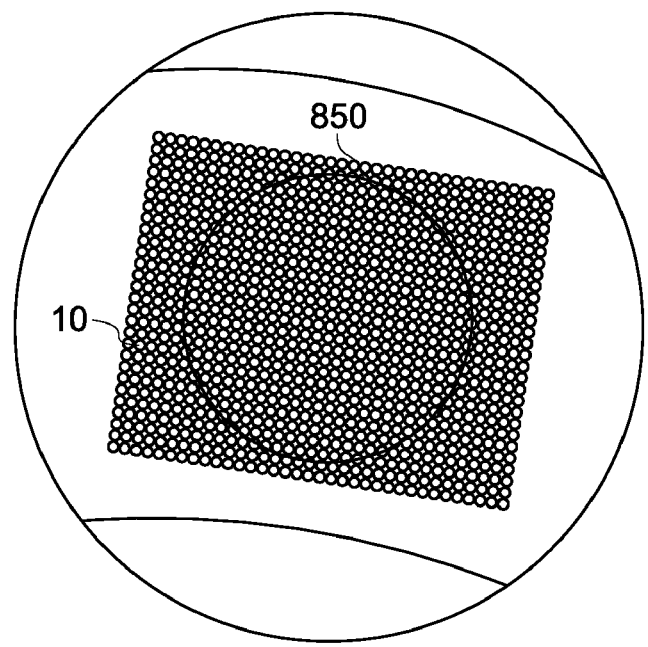
FIG. 12 is a close up schematic view illustrating an array of multilayer optics positioned in optical communication with a target focal spot in accordance with one embodiment.

It should be noted that the different combinations of diverging and substantially non-diverging photon sources illustrated in FIGS. 4-10 are merely examples of the various combinations that may be possible. The system should not be construed as limited by these combinations of photon sources (in conjunction with the optic devices). For example, in FIG. 5 all three photon sources may be radioactive sources instead of a combination of a radioactive source, an X-ray laser, and an X-ray source. Alternatively, the three photon sources may be a combination of two radioactive sources and a betatron X-ray source.http://en.wikipedia.org/wiki/File:Moon_gamma_rays_egret_instrument_cgro.jpg FIG. 12 illustrates an array of multilayer optics positioned such that at least one optic in the array is in optical communication with a focal spot on a target in an electron impact X-ray source, regardless of how the focal spot shifts due to target heating. The multilayer TIR optics may be mounted in the vacuum housing, either on a support structure within the housing, or as part of the vacuum housing itself spanning both the interior and exterior of the vacuum housing, or mounted exterior to the photon exit window of the housing. Alternatively, the multilayer TIR optics may be integral with the target, or mounted on or near the target (for transmission targets), or near the target (for reflection targets) in locations where the X-ray source focal spots are found.

It is known that X-ray source focal spots, such as 850, are not completely static and instead can move to some degree. It is understood that the array of multilayer optics 10 should be of sufficient size to compensate for the likely movement of the X-ray source focal spot 850. Further, although the array of multilayer optics 10 is shown to optically cover the entire target focal spot 850, it should be appreciated that the array may cover less than the entire target focal spot 850 and still function efficiently. In this manner, motion of the X-ray source focal spot due to target heating will not impact the alignment of the generated photon beam; this is a critical feature in systems that require accurate alignment of system components, such as X-ray diffraction imaging.

Figure 13:
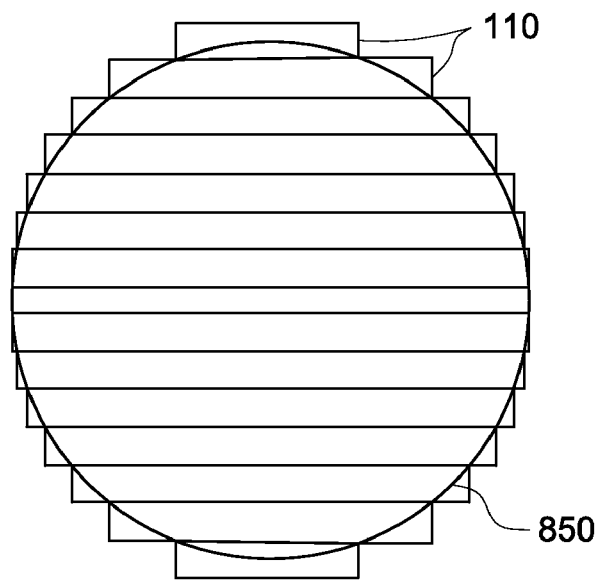
FIG. 13 is another schematic view illustrating an array of multilayer optics positioned in optical communication with a target focal spot in accordance with another embodiment of the invention.

With specific reference to FIG. 13, there is shown an array of multilayer TIR optics 110. Each of the multilayer TIR optics 110 is fabricated such that its width is sufficient to optically cover the extent of the X-ray source spot 850 with enough extra coverage to compensate for any likely movement of the X-ray source spot. Each of the multilayer TIR optics 110 can be fabricated to a certain width and stacked, or they can all be fabricated to the same width and stacked. The multilayer TIR optics 110 may be mounted on a window in the vacuum housing (not shown), either within the housing, or part of the window itself spanning both the interior and exterior of the vacuum house or on the exterior surface of the window outside of the housing. Alternatively, the multilayer TIR optics 110 may be integral with the target, or mounted on or near the target in locations where the X-ray source focal spots 850 are found.

The multilayer TIR optic is applicable to standard configurations of third-generation CT systems (where the X-ray tube and detector rotate about the imaging volume) as well as alternate configurations of third-generation technology, for example, with industrial CT configurations where the X-ray source and detector are held fixed and a stage rotates the object during data acquisition.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. For example, while the embodiments of the systems described with specific reference to FIGS. 4-11 refer to specific combinations of photon sources in conjunction with optical devices, such examples and the corresponding description was for ease of description only and it should be appreciated that any of the other combinations of photon sources and multilayer optic devices described herein can be incorporated as appropriate. Furthermore, the system encompasses approaches with more than two energies that may be provided by one or more of the photon sources, either emitted concurrently or sequentially or combinations thereof, where the photon sources are activated and deactivated as necessary to acquire the required imaging data. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected by Letters Patent of the United States is:

1. A system for producing at least one high flux photon beam, the system comprising:
two or more photon sources configured to produce photon beams; and
at least one first stage optic device coupled to at least one of said photon sources and providing at least one focused photon beam through total internal reflection;
wherein at least one of the photon beams and the focused photon beams are combined at a virtual focal spot.

2. The system of claim 1, wherein said photon sources include at least one diverging photon source or at least one substantially non-diverging photon source or combinations thereof.

3. The system as claimed in claim 2, wherein the diverging photon source comprises at least one of a radioactive source, a triboluminescent source, or an electron impact X-ray source, or combinations thereof.

4. The system as claimed in claim 3, wherein the electron sources in said impact X-ray sources comprise one or more of a spaced electron gun, a spaced hot cathode-based electron gun, a spaced cold cathode-based electron gun, or combinations thereof.

5. The system as claimed in claim 3, wherein the electron-impact X-ray sources comprise one or more different target materials.

6. The system as claimed in claim 3, wherein the radioactive source comprises one or more radioactive materials.

7. The system as claimed in claim 6, wherein the radioactive materials consist of one or more radioisotopes.

8. The system as claimed in claim 2, wherein the substantially non-diverging photon source comprises at least one of an X-ray laser, a synchrotron radiation source, a cyclotron radiation source, or combinations thereof.

9. The system as claimed in claim 1, further comprising a second stage optic optically coupled to the virtual focal spot and configured to generate a shaped beam, wherein the shaped beam comprises one of a parallel beam, focused beam, diverging beam, fan-shaped cone beam, stacked fan-shaped parallel beam, or combinations thereof.

10. The system as claimed in claim 9, wherein the second stage optic device comprises conformal solid phase layers, wherein interfaces between said solid phase layers are gapless and wherein said conformal solid phase layers include photon redirection regions for redirecting and transmitting the photon beams through total internal reflection.

11. The system as claimed in claim 9, wherein the shaped beam is focused to provide a focal spot that is 20 microns or smaller.

12. The system as claimed in claim 1, further comprising two or more virtual focal spots.

13. The system as claimed in claim 12, comprising additional photon sources to generate the additional focal spots.

14. The system as claimed in claim 12, wherein the photon beams and the focused photon beams are combined to form the two or more virtual focal spots.

15. The system as claimed in claim 1, wherein said first stage optic device comprises conformal solid phase layers, wherein interfaces between said solid phase layers are gapless and wherein said conformal solid phase layers include photon redirection regions for redirecting and transmitting the photon beams through total internal reflection.

16. The system as claimed in claim 1, wherein the photon beams and the focused photon beams comprise at least one of a monochromatic spectrum, a polychromatic spectrum, or combinations thereof.

17. The system as claimed in claim 1, wherein the at least one first stage optic device is coupled to at least one substantially non-diverging source.

18. The system as claimed in claim 1, wherein the two or more photon sources operate concurrently, or sequentially, or combinations thereof.

19. The system as claimed in claim 1, wherein the system is employed in a targeted imaging system, a diffraction-enhanced imaging system, a phase-contrast imaging system, a brachytherapy system, a computed tomography system, a radiography system, a backscatter imaging system, a radioisotope radiography system, an X-ray diffraction system, or an X-ray fluorescence system, or combinations thereof.

20. The system as claimed in claim 1, wherein a size of the virtual focal spot is 20 microns or smaller.

21. A high flux photon beam system, comprising:
two or more photon sources configured to produce photon beams;
at least one first stage optic device coupled to at least one of said photon sources and providing at least one focused photon beam through total internal reflection;
at least one virtual focal spot formed from the at least one focused photon beam, and at least one beam from the photon beams; and
at least one second stage optic device coupled to the at least one virtual focal spot and configured to generate a shaped photon beam.

22. The system as claimed in claim 21, wherein the photon beams are combined at the virtual focal spot.

23. The system as claimed in claim 21, wherein the optically focused photon beams are combined at two or more virtual focal spots, and wherein the at least one second stage optic device comprises a plurality of optic devices each coupled to at least one virtual focal spot.

24. A system for producing high flux photon beams, the system comprising:
two or more photon sources configured to produce photon beams,
wherein said photon sources include at least one non-diverging photon source, at least one diverging photon source, and combinations thereof;
wherein the at least one diverging source includes an optic device providing a focused photon beam through total internal reflection; and
the focused photon beam and photon beams from at least one of the other of the two or more photon sources are combined at a virtual focal spot.

25. The system as claimed in claim 24, further comprising a second-stage optic device coupled to the virtual focal spot and configured to generate a shaped photon beam.

26. The system as claimed in claim 25, wherein the shaped photon beam comprises one of a monochromatic spectrum, or a polychromatic spectrum, or combinations thereof.

27. The system as claimed in claim 24, wherein the photon beams and the focused photon beams comprise one of a monochromatic spectrum, or a polychromatic spectrum, or combinations thereof.

28. A system for producing at least one high flux photon beam, the system comprising:
at least two radioactive photon sources configured to produce photon beams; and
at least one first stage optic device coupled to one or more of said radioactive photon sources and providing focused photon beams, or parallel photon beams, or combinations thereof through total internal reflection;

wherein the focused photon beams, or parallel photon beams, or combinations thereof are combined at a virtual focal spot producing one or more shaped photon beams.

29. The system as claimed in claim 28, wherein the photon beam comprises one of a monochromatic spectrum, or a polychromatic spectrum, or combinations thereof.

30. The system as claimed in claim 28, wherein the shaped beam is one of a parallel beam, focused beam, diverging beam, fan-shaped cone beam, stacked fan-shaped parallel beam, and combinations thereof.

31. A system for producing at least one high flux photon beam, the system comprising:

two or more photon sources configured to produce photon beams combined at a virtual focal spot; and at least one optic device coupled to said virtual spot and configured to generate a shaped beam comprising one of a parallel beam, focused beam, diverging beam, a fan-shaped cone beam, a stacked fan-shaped parallel beam, or combinations thereof.

32. The system of claim 31, where in the optic device comprises a single optic device or a plurality of optic devices.

* * * * *